United States Patent [19]
Dong

[11] Patent Number: 5,593,448
[45] Date of Patent: Jan. 14, 1997

[54] GLENOID COMPONENT FOR SHOULDER PROSTHESIS AND IMPLANT METHOD

[75] Inventor: Nicholas N. G. Dong, Little Falls, N.J.

[73] Assignee: Osteonics Corp., Allendale, N.J.

[21] Appl. No.: 555,720

[22] Filed: Nov. 14, 1995

[51] Int. Cl.⁶ .................................................. A61F 2/40
[52] U.S. Cl. ................................ 623/19; 623/18; 606/86
[58] Field of Search ........................... 623/18, 19; 606/86

[56] References Cited

U.S. PATENT DOCUMENTS

| | | | |
|---|---|---|---|
| 3,694,820 | 10/1972 | Scales et al. | 623/19 |
| 3,979,778 | 9/1976 | Stroot | 623/19 |
| 4,003,095 | 1/1977 | Gristina | 623/19 |
| 4,045,825 | 9/1977 | Stroot | 623/19 |
| 4,045,826 | 9/1977 | Stroot | 623/19 |
| 4,106,130 | 8/1978 | Scales | 623/19 |
| 4,206,517 | 6/1980 | Pappas et al. | 623/19 |
| 4,261,062 | 4/1981 | Amstutz et al. | 623/19 |
| 4,964,865 | 10/1990 | Burkhead et al. | 623/19 |
| 4,986,833 | 1/1991 | Worland | 623/19 |
| 5,030,219 | 7/1991 | Matsen, III et al. | 623/19 |
| 5,032,132 | 7/1991 | Matsen, III et al. | 623/19 |
| 5,080,673 | 1/1992 | Burkhead et al. | 623/19 |

Primary Examiner—David Isabella
Attorney, Agent, or Firm—Arthur Jacob

[57] ABSTRACT

Affixation of a glenoid component of a prosthetic shoulder implant is enhanced and forces exerted upon the glenoid component during service are managed by the location and orientation of affixation pegs on the glenoid component, and especially the location of a medially extending superior affixation peg closely adjacent the superior edge of the glenoid component, and the offset orientation of an inferior affixation peg, relative to the superior affixation peg, the glenoid component including intermediate affixation pegs extending medially and spaced from one another in the anterior-posterior direction intermediate the superior affixation peg and the inferior affixation peg.

19 Claims, 4 Drawing Sheets

GLENOID COMPONENT FOR SHOULDER PROSTHESIS AND IMPLANT METHOD

The present invention relates generally to the implant of shoulder prostheses and pertains, more specifically, to a glenoid component for a shoulder prosthesis and a method for affixing the glenoid component to a scapula in an implant procedure.

Shoulder arthroplasty has become a highly successful procedure, and a variety of components is available for the implant of shoulder prostheses. Despite the success of the procedure, the incidence of separation of the glenoid component of a shoulder prosthesis from the scapula remains relatively high. From the standpoint of biomechanics, the stability of the glenoid component depends upon the amount of natural bone available at the implant site to serve as a foundation for affixation of the glenoid component on the scapula and the geometry of the existing natural bone available to resist the forces on the shoulder joint. The following are among the gleno/humeral joint forces which could affect the longevity of glenoid implants:

Superior loading force: An analysis of forces at the gleno/humeral joint in abduction indicates that the resultant joint force on the glenoid during abduction over the 30° to 60° range is located close to the superior edge of the glenoid. The magnitude of the force increases linearly as the abduction angle increases, with the force peaking at 90° abduction. The higher superior loading force creates a rocking moment causing the inferior portion of the glenoid component to lift, resulting in separation from the scapula, the mode of failure observed most often in prosthetic shoulder implants.

Straight compression load: The compression load increases linearly from 0° to 90° abduction, and then is reduced with further abduction from 90° to 150°.

Inferior loading force: The inferior loading force is observed to occur in the range of 0° to 30° abduction and is far less than the superior loading force, or the straight compression load.

Shear force: The shear force occurs mainly from subluxation of the humeral head.

Anterior/posterior loading forces: These forces basically are out-of-plane components of the superior loading force, the straight compression force and the inferior loading force.

Rotational force: Rotational forces are induced by the rotational motion of the humeral head.

The present invention provides a glenoid component, and a method for affixing the glenoid component to a scapula in an implant procedure, which address loading conditions encountered as a result of the above forces to achieve better affixation. As such, the present invention attains several objects and advantages, some of which are summarized as follows: Provides a glenoid component with superior and inferior affixation peg location and orientation for placement within the scapula at locations where maximum amounts of natural bone are available for effective anchoring of the pegs and for minimal risk of deleterious bone perforation, and for managing moments exerted on the glenoid component as a result of forces encountered during service, for more effective resistance to separation of the glenoid component from the scapula; employs a full complement of affixation pegs, combined with an overall curved affixation surface, for resisting shear forces and rocking of the glenoid component on the scapula, while preserving existing natural bone at the implant site; enables the economical employment of a unitary, one-piece glenoid component, preferably constructed of a synthetic polymeric material; attains effective affixation of a glenoid component to the scapula, utilizing cemented affixation techniques; attains mechanical interlocking of the glenoid component with the scapula, independent of cemented affixation; and provides exemplary performance in an implanted glenoid component over an extended service life.

The above objects and advantages, as well as further objects and advantages, are attained by the present invention which may be described briefly as a glenoid component for affixation to a scapula to provide a bearing for a humeral head in a shoulder prosthesis, the glenoid component comprising: a glenoid member extending in a superior-inferior direction and having a superior edge, an inferior edge, a lateral face and a medial face; bearing means at the lateral face for providing the bearing for the humeral head; an affixation surface along the medial face for affixing the glenoid member to the scapula; a superior affixation peg integral with the glenoid member and projecting from the medial face of the glenoid member in a medial direction, essentially perpendicular to the superior-inferior direction, the superior affixation peg having a root at the glenoid member, the root being located closely adjacent the superior edge of the glenoid member for placement of the superior affixation peg at a superior location in the scapula, the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula; and an inferior affixation peg integral with the glenoid member and projecting from the medial face of the glenoid member in an offset direction making an acute angle with the medial direction of the superior affixation peg, in a medial-inferior direction, the inferior affixation peg being located adjacent the inferior edge of the glenoid member for placement of the inferior affixation peg at an inferior location in the scapula, the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid member in response to the superior forces.

In addition, the invention includes a glenoid component for affixation to a scapula to provide a bearing for a humeral head in a shoulder prosthesis, the glenoid component comprising: a glenoid member extending in a superior-inferior direction and having a superior edge, an inferior edge, a lateral face and a medial face; bearing means at the lateral face for providing the bearing for the humeral head; an affixation surface along the medial face for affixing the glenoid member to the scapula; a superior affixation peg projecting from the medial face of the glenoid member in a medial direction, essentially perpendicular to the superior-inferior direction, the superior affixation peg having a root at the glenoid member, the root being located closely adjacent the superior edge of the glenoid member for placement of the superior affixation peg at a superior location in the scapula, the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula; an inferior affixation peg projecting from the medial face of the glenoid member in an offset direction making an acute angle with the medial direction of the superior affixation peg, in a medial-inferior direction, the inferior affixation peg being located adjacent the inferior edge of the glenoid member for placement of the inferior affixation peg at an inferior location in the scapula, the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid member in response to the superior forces; and at least one intermediate affixation peg projecting from the medial face of the glenoid member in a medial direction, generally parallel to the superior affixation peg, intermediate the superior affixation peg and the inferior affixation peg.

Further, the invention includes a method for affixing a glenoid component to a scapula to provide a bearing for a humeral head in a shoulder prosthesis, the glenoid component including a glenoid member extending in a superior-inferior direction and having a superior edge, an inferior edge, a lateral face and a medial face, the method comprising: providing a superior affixation peg integral with and projecting from the medial face of the glenoid member in a medial direction, essentially perpendicular to the superior-inferior direction, the superior affixation peg having a root at the glenoid member, the root being located closely adjacent the superior edge of the glenoid member; providing an inferior affixation peg integral with and projecting from the medial face of the glenoid member in an offset direction making an acute angle with the medial direction of the superior affixation peg, in a medial-inferior direction, the inferior affixation peg being located adjacent the inferior edge of the glenoid member; placing the inferior affixation peg at an inferior location in the scapula; and subsequently placing the superior affixation peg at a superior location in the scapula; the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula; and the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid in response to the superior forces.

The invention will be understood more fully, while still further objects and advantages will become apparent, in the following detailed description of preferred embodiments of the invention illustrated in the accompanying drawing, in which.

Figure 1:
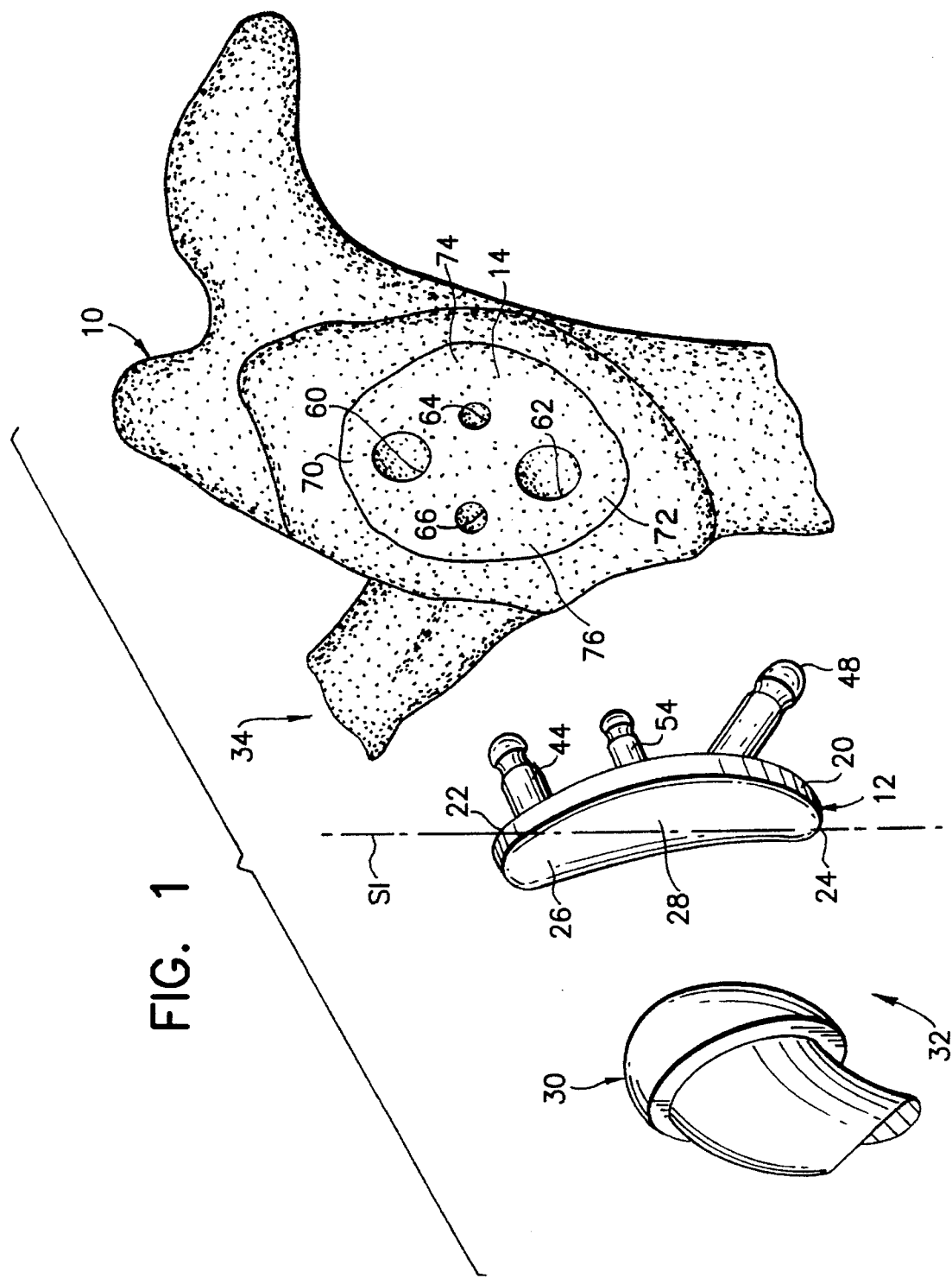
FIG. 1 is a pictorial perspective view of a glenoid component constructed in accordance with the present invention, about to be affixed to a scapula in accordance with the method of the invention.

Referring now to the drawing, and especially to FIG. 1 thereof, a scapula 10 has been prepared for the affixation of a glenoid component 12 to the scapula 10 at the glenoid surface 14 of the scapula 10. Glenoid component 12 is constructed in accordance with the present invention and is seen to include a glenoid member 20 extending in a superior-inferior direction SI, that is, in upward and downward directions, between an upper, or superior edge 22, and a lower, or inferior edge 24. An obverse, or lateral face 26 at the front of the glenoid member 20 has a concave contour configuration and provides bearing means in the form of a concave bearing surface 28 for the reception of a humeral head, shown diagrammatically at 30 as a part of a shoulder prosthesis 32 being implanted at the implant site 34.

Figure 2:
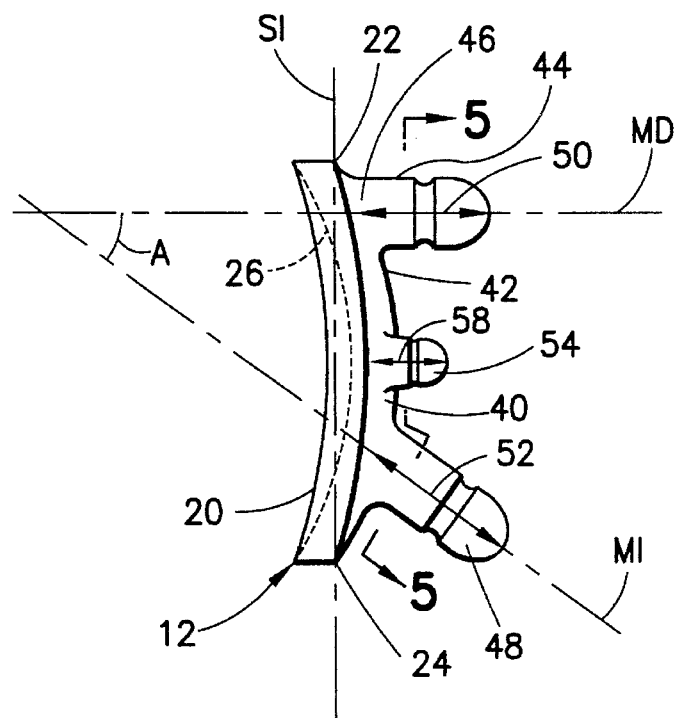
FIG. 2 is a side elevational view of the glenoid component.
Figure 3:
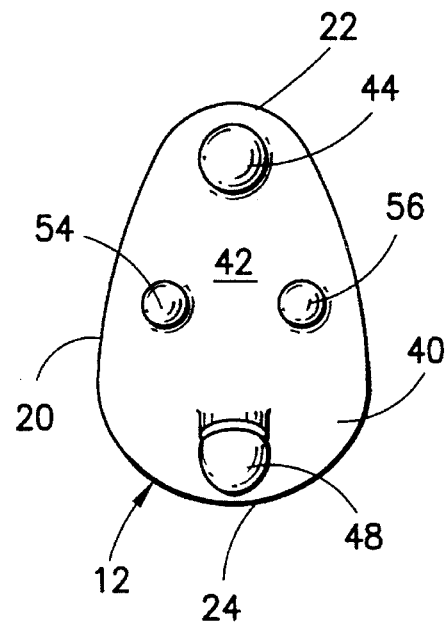
FIG. 3 is a rear elevational view of the glenoid component.
Figure 4:
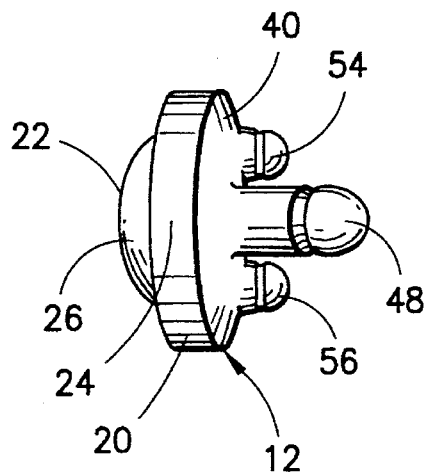
FIG. 4 is a bottom plan view of the glenoid component.

Turning now to FIGS. 2 through 4, glenoid member 20 includes a reverse, or medial face 40, which has a generally convex contour configuration, and an affixation surface 42 extending along the medial face 40 for affixing the glenoid member 20 to the scapula 10. An upper, or superior affixation peg 44 projects from the medial face 40 in a medial direction MD, essentially perpendicular to the superior-inferior direction SI, and is integral with the glenoid member 20 at a root 46 located closely adjacent the superior edge 22 of the glenoid member 20. A lower, or inferior affixation peg 48 also projects from the medial face 40 of the glenoid member 20 and is oriented in an offset direction, relative to the superior affixation peg 44, which offset direction makes an acute angle A with the medial direction MD to extend in a generally medial and downward direction, characterized as a medial-inferior direction MI. The inferior affixation peg 48 is located adjacent the inferior edge 24 of the glenoid member 20 and is integral with the glenoid member 20. Superior affixation peg 44 has a longitudinal length 50 and inferior affixation peg 48 has a longitudinal length 52 which is somewhat greater than longitudinal length 50. In the preferred orientation of inferior affixation peg 48, angle A is about 30°.

In the preferred embodiment, glenoid component 12 includes at least one, and preferably two intermediate affixation pegs 54 and 56, placed intermediate the superior and inferior affixation pegs 44 and 48, and projecting from the medial face 40 of the glenoid member 20 in medial directions essentially parallel with the medial direction MD. Intermediate affixation pegs 54 and 56 are spaced apart in the anterior-posterior direction, with intermediate affixation peg 54 being an anterior affixation peg and intermediate affixation peg 56 being a posterior affixation peg. Intermediate affixation pegs 54 and 56 each have a longitudinal length 58 which is less than the longitudinal lengths 50 and 52 of the superior and inferior affixation pins 44 and 48, respectively. In the preferred construction, glenoid component 12 is constructed in a one-piece member of synthetic polymeric material, with the affixation pegs 44, 48, 54 and 56 unitary with glenoid member 20, the preferred material being ultra high molecular weight polyethylene.

Glenoid component 12 is affixed to scapula 10 at the implant site 34 by cementing the glenoid component 12 in place in the scapula 10, by mechanically interlocking the glenoid component 12 within the scapula 10, or by a combination of both mechanical interlocking and cemented affixation, all as described below. As best seen in FIG. 1, the scapula is prepared by drilling holes 60, 62, 64 and 66 in the scapula 10, at the implant site 34, for the reception of the affixation pegs 44, 48, 54 and 56, respectively. The location and orientation of the affixation pegs 44, 48, 54 and 56 enables placement of the holes 60, 62, 64 and 66 at locations where the geometry and mass of the natural bone make available the maximum amount of bone for the reception of the affixation pegs. Thus, the superior affixation peg 44 is engaged with a superior portion 70 of the scapula 10, which superior portion 70 provides a geometric shape and extent of natural bone best engaged by the particular location and orientation of superior affixation peg 44; that is, the amount of bone available along the medial direction MD enables the drilling of the hole 60 in the portion 70 to provide for secure anchoring of the superior affixation peg 44 in the portion 70, with the attainment of maximum fixation strength, while avoiding deleterious perforation of the portion 70 in the completion of hole 60.

Likewise, the inferior affixation peg 48 is engaged with an inferior portion 72 of the scapula 10, which inferior portion 72 provides the geometry and amount of natural bone best engaged by the location and orientation of inferior affixation peg 48; that is, the amount of bone available along the offset, medial-inferior direction MI enables the drilling of the hole 62 in the portion 72 to provide for the secure anchoring of the inferior affixation peg 48 in the portion 72 with maximum affixation strength, while avoiding deleterious perforation of the portion 72 in the completion of hole 62. Moreover, the location of the inferior affixation peg 48 along the medial-inferior direction MI places the inferior affixation peg 48 within denser cortical bone, providing greater affixation strength, particularly in resistance to rocking in response to superior loading forces. In a similar manner, the holes 64 and 66 are located in corresponding intermediate portions 74 and 76 of the scapula 10, for the reception of the intermediate affixation pegs 54 and 56, respectively. The intermediate portions 74 and 76 provide peripheral denser glenoid sub-condylar bone for best anchoring the intermediate affixation pegs 54 and 56.

Figure 5:
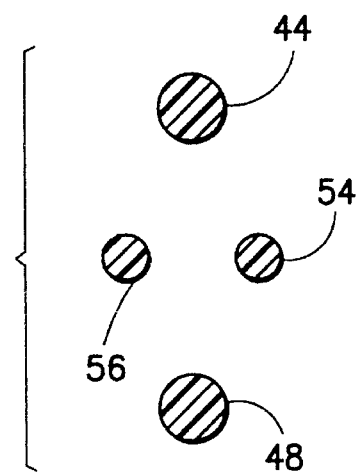
FIG. 5 is a cross-sectional view taken along line 5—5 of FIG. 2.
Figure 6:
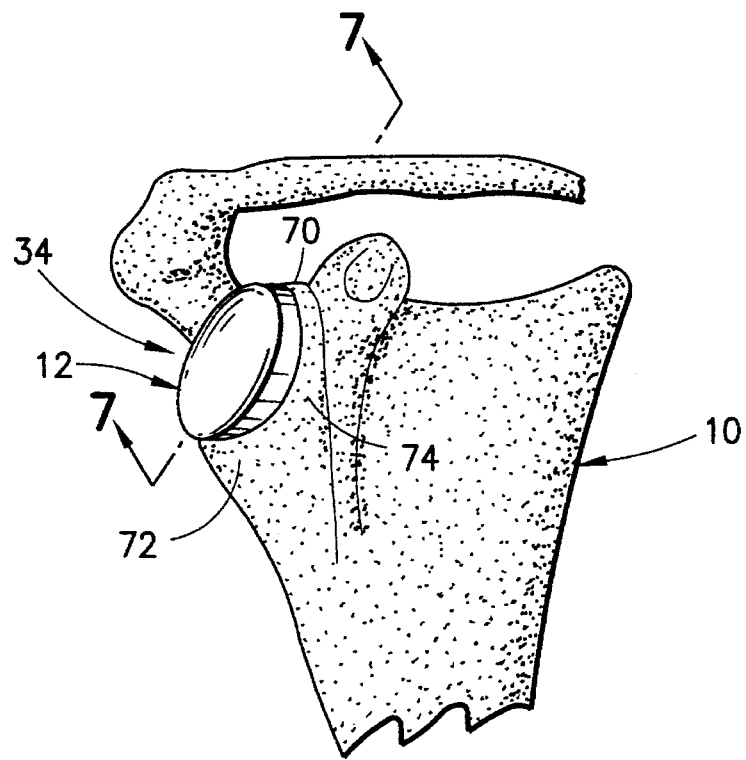
FIG. 6 is a pictorial perspective view showing the glenoid component affixed to the scapula.
Figure 7:
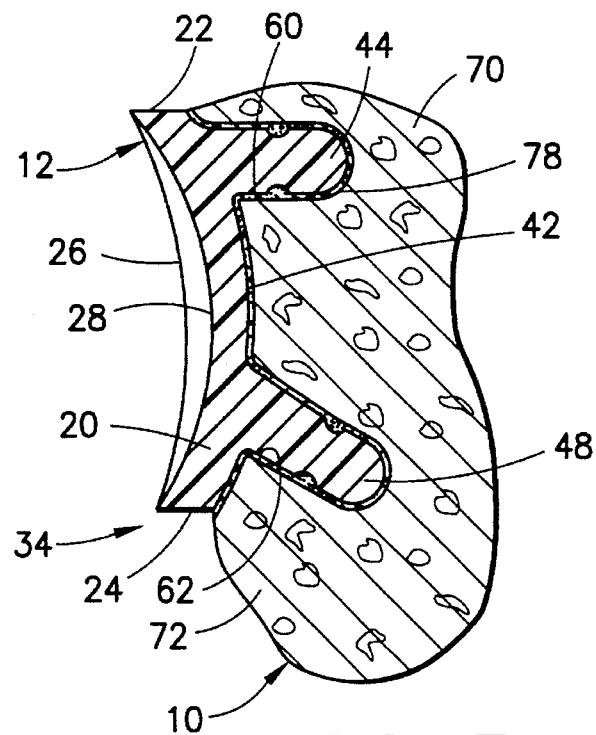
FIG. 7 is an enlarged cross-sectional view taken along line 7—7 of FIG. 6.
Figure 8:
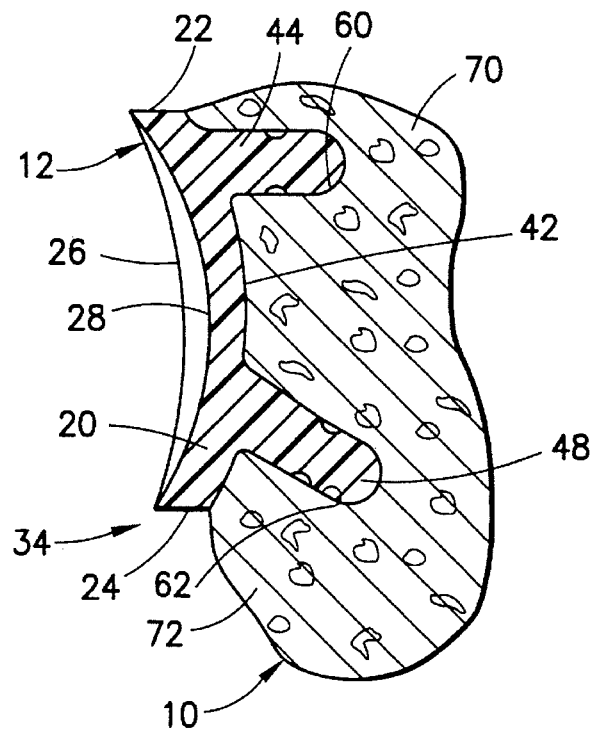
FIG. 8 is a cross-sectional view similar to FIG. 7, but showing an alternate affixation arrangement.

Turning now to FIGS. 5 through 7, where a cemented affixation is employed, the superior affixation peg 44 and the inferior affixation peg 48 are fitted, respectively, into holes 60 and 62, and a cement mantle 78 affixes the glenoid component 12 in place in the scapula 10. However, the location, orientation and relative lengths of superior affixation peg 44 and inferior affixation peg 48, coupled with the somewhat resilient nature of the material of the glenoid member 20, enables an alternate securement in the form of a mechanical locking arrangement between the glenoid component 12 and the scapula 10. Thus, as seen in FIG. 8, by first inserting the offset, relatively longer inferior affixation peg 48 into hole 62, and then flexing glenoid member 20 to locate the superior affixation peg 44 at hole 60, the superior affixation peg 44 is snapped into hole 60 and the angular offset relationship between the integral shorter superior affixation peg 44 and the integral offset longer inferior affixation peg 48 retains the glenoid component 12 in place in the scapula 10, without cement. In such an arrangement, superior affixation peg 44 is fitted relatively tightly into hole 60. As another alternative, both a snap-in mechanical interlocking arrangement and a cement mantle, each as described above, can be employed in combination to affix the glenoid component 12 within the scapula 10. For either of the above described cemented affixation or mechanical interlocking arrangement, the preferred configuration for the superior affixation peg 44 and for the inferior affixation peg 48 is the illustrated cylindrical configuration wherein the affixation pegs have an essentially circular cross-sectional configuration, as shown in FIGS. 2 through 5. The cylindrical configuration, with the essentially circular cross-sectional configuration, assures an appropriate fit with ease of preparation and reduction of stresses.

Figure 9:
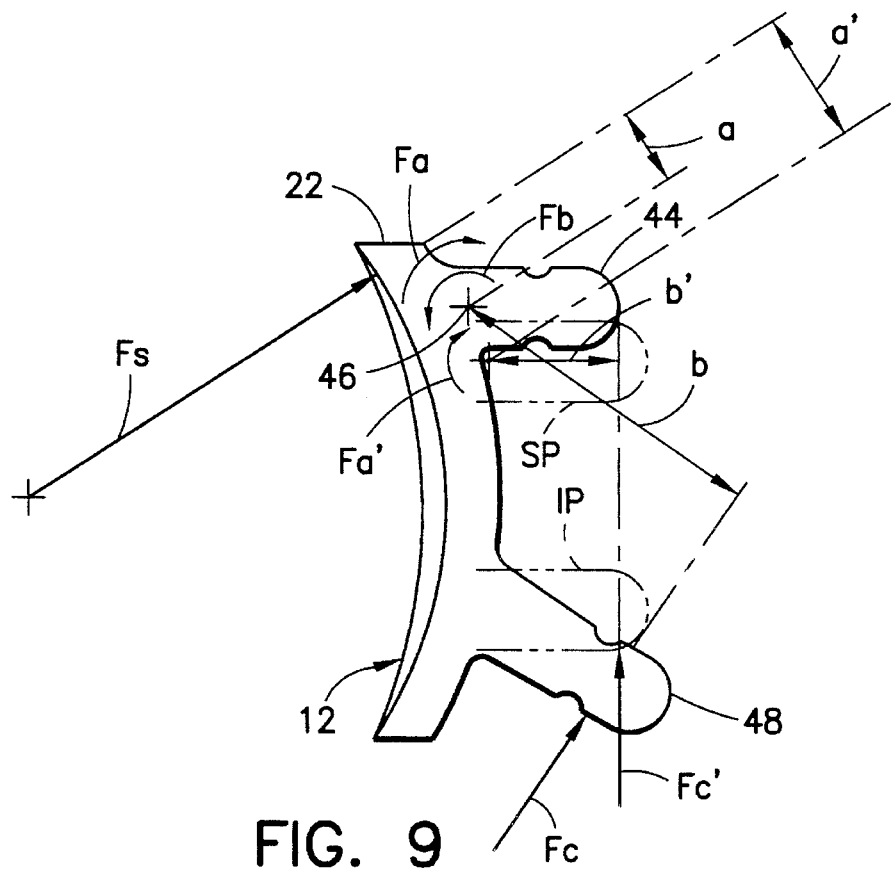
FIG. 9 is a schematic force diagram showing forces encountered during service.

The location and orientation of the superior affixation peg 44 and the inferior affixation peg 48, on the glenoid member 20 and relative to one another, not only direct the affixation pegs 44 and 48 into the corresponding portions 70 and 72 of the scapula 10 of maximum natural bone for maximum affixation strength, and enable the above-described mechanical interlocking arrangement, but also provide for effective management of forces encountered during service. Thus, as illustrated in FIG. 9, superior loading force Fs is shown acting upon the glenoid component 12 at the superior edge 22 of the glenoid member 20 and, as a result of moment arm a, creates a superior rocking moment Fa about the root 46 of the superior affixation peg 44. An inferior counterbalancing force Fc at inferior affixation peg 48 acts through a moment arm b to establish a counterbalancing moment Fb. The location and orientation of the superior and inferior affixation pegs 44 and 48 render the moment arm a much shorter than the moment arm b, enabling a relatively lower magnitude inferior counterbalancing force Fc to counterbalance a higher magnitude superior loading force Fs in the prevention of superior rocking.

In more conventional arrangements, as shown in phantom in FIG. 9, wherein a superior affixation peg SP is spaced away from the superior edge 22 and an inferior affixation peg IP extends parallel with the superior affixation peg SP, the superior loading force Fs acts through a moment arm a', which is longer than moment arm a, and a counterbalancing force Fc' acts through a moment arm b', which is shorter than moment arm b. In order to counterbalance force Fs, and the superior rocking moment Fa', the counterbalancing force Fc' must be considerably greater than force Fc. Hence, a greater force Fc' is required in the conventional arrangement to resist superior rocking and concomitant separation of the glenoid component from the scapula. Accordingly, the placement of the superior affixation peg 44 closely adjacent the superior edge 22 of the glenoid member 20, and the placement and offset orientation of the inferior affixation peg 48, attain a much improved management of the forces encountered during service, enabling lesser counterbalancing forces, and concomitant reduced stresses, in order to maintain stability in the implanted glenoid component 12.

The anterior and posterior intermediate affixation pegs 54 and 56 provide a full complement of affixation pegs in the form of an array of four affixation pegs 44, 48, 54 and 56 for better resistance to shear, rotational forces and anterior/posterior rocking, especially as a result of additional interdigitation with the bone and greater bonding.

It will be apparent that the above-described construction and method attains the objects and advantages summarized above, namely: Provides a glenoid component with superior and inferior affixation peg location and orientation for placement within the scapula at locations where maximum amounts of natural bone are available for locations where maximum amounts of natural bone are available for effective anchoring of the pegs and for minimal risk of deleterious bone perforation, and for managing moments exerted on the glenoid component as a result of forces encountered during service, for more effective resistance to separation of the glenoid component from the scapula; employs a full complement of affixation pegs, combined with an overall curved affixation surface, for resisting shear forces and a rocking of the glenoid component on the scapula, while preserving existing natural bone at the implant site; enables the economical employment of a unitary, one-piece glenoid component, preferably constructed of a synthetic polymeric material; attains effective affixation of a glenoid component to the scapula, utilizing cemented affixation techniques; attains mechanical interlocking of the glenoid component with the scapula, independent of cemented affixation; and provides exemplary performance in an implanted glenoid component over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A glenoid component for affixation to a scapula to provide a bearing for a humeral head in a shoulder prosthesis, the glenoid component comprising:

a glenoid member extending in a superior-inferior direction and having a superior edge, an inferior edge, a lateral face and a medial face;

bearing means at the lateral face for providing the bearing for the humeral head;

an affixation surface along the medial face for affixing the glenoid member to the scapula;

a superior affixation peg integral with the glenoid member and projecting from the medial face of the glenoid member in a medial direction, essentially perpendicular to the superior-inferior direction, the superior affixation peg having a root at the glenoid member, the root being located closely adjacent the superior edge of the glenoid member for placement of the superior affixation peg at a superior location in the scapula, the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula; and an inferior affixation peg integral with the glenoid member and projecting from the medial face of the glenoid member in an offset direction making an acute angle with the medial direction of the superior affixation peg, in a medial-inferior direction, the inferior affixation peg being located adjacent the inferior edge of the glenoid member for placement of the inferior affixation peg at an inferior location in the scapula, the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid member in response to the superior forces.

2. The invention of claim 1 wherein the offset direction of the inferior affixation peg makes an acute angle of about 30° with the medial direction of the superior affixation peg.

3. The invention of claim 1 wherein the superior affixation peg has a first length, and the inferior affixation peg has a second length greater than the first length.

4. The invention of claim 3 wherein the superior affixation peg is cylindrical and includes an essentially circular cross-sectional configuration.

5. The invention of claim 4 wherein the inferior affixation peg is cylindrical and includes an essentially circular cross-sectional configuration.

6. The invention of claim 1 wherein the superior affixation peg and the inferior affixation peg are unitary with the glenoid member in a one-piece glenoid component.

7. The invention of claim 6 wherein the one-piece glenoid component is constructed of a synthetic polymeric material.

8. The invention of claim 7 wherein the synthetic polymeric material is an ultra high molecular weight polyethylene.

9. The invention of claim 1 wherein the affixation surface is convex.

10. A glenoid component for affixation to a scapula to provide a bearing for a humeral head in a shoulder prosthesis, the glenoid component comprising:

a glenoid member extending in a superior-inferior direction and having a superior edge, an inferior edge, a lateral face and a medial face;

bearing means at the lateral face for providing the bearing for the humeral head;

an affixation surface along the medial face for affixing the glenoid member to the scapula;

a superior affixation peg projecting from the medial face of the glenoid member in a medial direction, essentially perpendicular to the superior-inferior direction, the superior affixation peg having a root at the glenoid member, the root being located closely adjacent the superior edge of the glenoid member for placement of the superior affixation peg at a superior location in the scapula, the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula;

an inferior affixation peg projecting from the medial face of the glenoid member in an offset direction making an acute angle with the medial direction of the superior affixation peg, in a medial-inferior direction, the inferior affixation peg being located adjacent the inferior edge of the glenoid member for placement of the inferior affixation peg at an inferior location in the scapula, the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid member in response to the superior forces; and at least one intermediate affixation peg projecting from the medial face of the glenoid member in a medial direction, generally parallel to the superior affixation peg, intermediate the superior affixation peg and the inferior affixation peg.

11. The invention of claim 7 including at least two intermediate pegs projecting from the medial face of the glenoid member in a medial direction, generally parallel to the superior affixation peg, intermediate the superior affixation peg and the inferior affixation peg, the intermediate affixation pegs being spaced from one another in the anterior-posterior direction.

12. The invention of claim 11 wherein the superior affixation peg has a first length, the inferior affixation peg has a second length, and the intermediate affixation pegs each have a third length less than either one of the first length and the second length.

13. The invention of claim 12 wherein the superior affixation peg, the inferior affixation peg, and the intermediate affixation pegs each are cylindrical, each including an essentially circular cross-sectional configuration.

14. The invention of claim 10 wherein the superior affixation peg, the inferior affixation peg, and each intermediate affixation peg are unitary with the glenoid member in a one-piece glenoid component.

15. The invention of claim 14 wherein the one-piece glenoid component is constructed of a synthetic polymeric material.

16. The invention of claim 15 wherein the synthetic polymeric material is an ultra high molecular weight polyethylene.

17. The invention of claim 10 wherein the affixation surface is convex.

18. A method for affixing a glenoid component to a scapula to provide a bearing for a humeral head in a shoulder prosthesis, the glenoid component including a glenoid member extending in a superior-inferior direction and having a superior edge, an inferior edge, a lateral face and a medial face, the method comprising:

providing a superior affixation peg integral with and projecting from the medial face of the glenoid member in a medial direction, essentially perpendicular to the superior-inferior direction, the superior affixation peg having a root at the glenoid member, the root being located closely adjacent the superior edge of the glenoid member;

providing an inferior affixation peg integral with and projecting from the medial face of the glenoid member in an offset direction making an acute angle with the medial direction of the superior affixation peg, in a medial-inferior direction, the inferior affixation peg being located adjacent the inferior edge of the glenoid member;

placing the inferior affixation peg at an inferior location in the scapula; and subsequently placing the superior affixation peg at a superior location in the scapula;

the superior location providing maximum available bone for anchoring the superior affixation peg in the scapula while establishing a minimal superior moment arm for superior forces acting upon the glenoid member and tending to rock the glenoid member about the root, when the glenoid member is affixed to the scapula; and the inferior location providing maximum available bone for anchoring the inferior affixation peg in the scapula while establishing an inferior moment arm for inferior counterbalancing forces, with the inferior moment arm being greater than the superior moment arm such that upon affixation of the glenoid member to the scapula and subjecting the glenoid member to the superior forces, the inferior moment arm enables lesser inferior counterbalancing forces to counterbalance greater superior forces for resisting said rocking of the glenoid in response to the superior forces.

19. The invention of claim 18 wherein the offset direction of the inferior affixation peg makes an acute angle of about 30° with the medial direction of the superior affixation peg.

* * * * *